(12) United States Patent
Rothe et al.

(10) Patent No.: US 6,187,557 B1
(45) Date of Patent: Feb. 13, 2001

(54) C-IAP1 AND C-IAP2: INHIBITORS OF APOPTOSIS

(75) Inventors: Mike Rothe, San Mateo; David V. Goeddel, Hillsborough, both of CA (US)

(73) Assignee: Tularik Inc., South San Francisco, CA (US)

(*) Notice: Under 35 U.S.C. 154(b), the term of this patent shall be extended for 0 days.

(21) Appl. No.: 08/569,749

(22) Filed: Dec. 8, 1995

Related U.S. Application Data

(63) Continuation of application No. 08/512,946, filed on Dec. 8, 1995, now abandoned.

(51) Int. Cl.[7] .............................. C12P 21/06; C12P 21/04; C12N 15/09
(52) U.S. Cl. .................. 435/69.1; 435/69.2; 435/70.1
(58) Field of Search .............................. 514/44; 435/69.1, 435/375, 320.1, 7.1, 6; 536/24.3, 23.1; 935/34; 424/93.21

(56) References Cited

PUBLICATIONS

Marshall, E (1995) Science 269: 1050–1055.*
Miller et al (1995) Targeted Gene Therapy 9: 190–199.*
Birnbaum et al (1994) J. Virol. 68: 2521–2528.*
M Rothe et al (1995) Cell 83: 1243–1252.
A Fernandez et al (1994) Cancer Bulletin 46: 153–160.
DL Vaux et al (1994) Proc Natl Acad Sci USA 93: 2239–2244.
L Hillier et al (Apr. 5, 1995) EST accession No. R07927. Accessed Feb. 21, 1997.
L Hillier et al (Mar. 27, 1995) EST accession No. T96284. Accessed Feb. 21, 1997.

* cited by examiner

*Primary Examiner*—Karen M. Hauda
*Assistant Examiner*—Joseph T. Woitach
(74) *Attorney, Agent, or Firm*—Richard Aron Osman

(57) ABSTRACT

The invention provides methods and compositions relating to novel human cellular inhibitor of apoptosis proteins (c-IAP1/2) comprising a series of defined structural domain repeats and/or a RING finger domain; in particular, at least two of: a particular first domain repeat, a particular second domain repeat, and a particular third domain repeat, and/or a particular RING finger domain. The proteins provide a c-IAP specific function, with preferred proteins being capable of modulating the induction of apoptosis; for example, by binding a human tumor necrosis factor receptor associated factor (TRAF). The compositions include nucleic acids which encode the subject c-IAP and hybridization probes and primers capable of hybridizing with the disclosed c-IAP genes.

17 Claims, No Drawings

C-IAP1 AND C-IAP2: INHIBITORS OF APOPTOSIS

CROSS-REFERENCE TO RELATED APPLICATION

This application is a continuation under 35 USC 120 of U.S. Ser. No. 08/512,946 filed Dec. 08, 1995, now abandoned.

INTRODUCTION

Field of the Invention

The field of this invention is human proteins involved in the inhibition of apoptosis, or programmed cell death.

Background

Cellular apoptosis, or programmed cell death, may be initiated by a variety of different stimuli including viral infection, certain cell-culture conditions, cell-cell signaling, cytokines, etc. Elucidation of signal transduction pathways leading to apoptosis would provide valuable insight into a variety of pathogenic mechanisms. Accordingly, the ability to exogenously modulate the induction of apoptosis would yield therapeutic application for numerous clinical indications. In addition, components of such pathways would provide valuable targets for automated, cost-effective, high throughput drug screening and hence would have immediate application in domestic and international pharmaceutical and biotechnology drug development programs.

Relevant Literature

Rothe et al. (1994) Cell 78, 681–692, report the existence of tumor necrosis factor (TNF) receptor associated proteins which co-immunoprecipitate with a TNF receptor; see also Rothe, et al., pending U.S. patent application Ser. No. 08/446,915. Roy, et al. (1995) Cell 80, 167–178 disclose the gene for a human neuronal apoptosis inhibitory protein. Birnbaum et al. (1994) J Virol 68, 2521–2528 disclose an inhibitor of apoptosis (iap) gene, Op-iap from the Orgyia pseudotsugata nuclear polyhedrosis virus (OpMNPV) with sequence similarity to two other viral genes: Cp-iap derived from Cydia pomonella granulosis virus (CpGV), and iap derived from the Autographa californica nuclear polyhedrosis virus (AcMNPV). Clem and Miller (1994), in Apoptosis II: The Molecular Basis of Apoptosis in Disease, pp 89–110, Cold Spring Harbor Laboratory Press, provide a recent review of apoptosis regulation by insect viruses.

SUMMARY OF THE INVENTION

The invention provides methods and compositions relating to novel human cellular inhibitor of apoptosis proteins (c-IAP). The subject proteins comprise a series of defined structural domain repeats and/or a RING finger domain; in particular, at least two of a first domain repeat comprising SEQUENCE ID NO: 5 or 6; a second domain repeat comprising SEQUENCE ID NO: 7 or 8; and a third domain repeat comprising SEQUENCE ID NO: 9 or 10; and/or a RING finger domain comprising SEQUENCE ID NO: 11 or 12, or a consensus sequences derived from these human genes. The proteins provide a c-IAP specific function, with preferred proteins being capable of modulating the induction of apoptosis; for example, by binding a human tumor necrosis factor receptor associated factor, TRAF. The compositions include nucleic acids which encode the subject c-IAP and hybridization probes and primers capable of hybridizing with the disclosed c-IAP genes.

The invention includes methods of using the subject compositions in therapy (e.g. gene therapy to enhance expression of a c-IAP gene), in diagnosis (e.g. genetic hybridization screens for c-IAP gene mutations, and in the biopharmaceutical industry (e.g. reagents for increasing yields of recombinant protein by enhancing host cell survival in culture, for screening chemical libraries for lead compounds for a pharmacological agent useful in the diagnosis or treatment of disease associated with apoptosis regulation, etc.).

DETAILED DESCRIPTION OF THE INVENTION

The invention provides methods and compositions relating to novel cellular inhibitor of apoptosis proteins (c-IAPs). The nucleotide sequence of a natural cDNA encoding human c-IAP is shown as SEQUENCE ID NO: 1 and the full conceptual translate is shown as SEQUENCE ID NO:2. The nucleotide sequence of another natural cDNA encoding human c-IAP2 is shown as SEQUENCE ID NO:3 and the full conceptual translate is shown as SEQUENCE ID NO:4. The human c-IAPs of the invention include incomplete translates of SEQUENCE ID NOS:1 and 3 or deletions mutants of SEQUENCE ID NOS: 2 and/or 4, which translates or deletions mutants have at least one of the human c-LAP specific activities described herein. In addition, the invention provides nonhuman mammalian homologs of the disclosed human c-IAPs. These homologs are encoded by natural cDNAs which are capable of specifically hybridizing with one or more of the disclosed human cDNAs under hybridization conditions describe below and are isolated using the methods and reagents described herein. For example, the amino acid sequence of a murine homolog of c-IAP1, and the sequence its cDNA are shown in SEQUENCE ID NOS: 14 and 13.

The subject proteins comprise a series of defined structural domain repeats and/or a RING finger domain shown to be necessary for human c-IAP specific function; generally including at least two of: a first domain repeat comprising SEQUENCE ID NO: 5, 6 or a consensus of 5 and 6, a second domain repeat comprising SEQUENCE ID NO: 7, 8 or a consensus of 7 and 8, and a third domain repeat comprising SEQUENCE ID NO: 9, 10 or a consensus of 9 and 10; and/or a RING finger domain comprising SEQUENCE ID NO: 11, 12 or a consensus of 11 and 12. Preferred domain repeat containing c-IAPs contain each of the three domain repeats. More preferred c-IAPs comprise the three domain repeats and the C-terminal RING finger. To secure or optimize the requisite function for the protein, the repeats are usually preceded (N-terminally) and separated by intervening regions of about 10 to about 100 residues, which regions preferably derive from those found in the natural c-IAP1 and c-IAP2 translates. Similarly, the RING finger domain of RING finger domain containing c-IAPs containing proteins is usually preceded by an N-terminal region of about 10 to 300 residues, usually 100 to 300 residues, which region preferably derives from those found in the natural c-IAP1 and c-IAP2 translates.

The proteins provide a human c-IAP1 or c-IAP2 (c-IAP1/2) specific activity or function which may be determined by convenient in vitro, cell-based, or in vivo assays. Preferred proteins are capable of modulating the induction of apoptosis. Such activity or function may be demonstrated in cell culture (e.g. cell transfections) or in animals (e.g. in vivo gene therapy, transgenics). c-IAP1/2 specific function can also be demonstrated by specific binding to a c-IAP1/2 specific binding target, including natural binding targets and nonnatural targets such as c-IAP1/2 specific antibodies. For example, c-IAPs comprising at least two of SEQUENCE ID NOS: 6, 7 and 8 are capable of specifically binding human tumor necrosis factor receptor associated factors 1 and 2 (TRAFI and TRAF2) in simple in vitro binding assays. Finally, specific function can be assayed immunologically by the ability of the subject protein to elicit a c-IAP1/2 specific antibody in a rodent or rabbit. Generally, human c-IAP1/2-specificity of the binding agent is shown by binding equilibrium constants (usually at least about $10^7 M^{-1}$, preferably at least about $10^8 M^{-1}$, more preferably at least about $10^9 M^{-1}$). A wide variety of cell-based and cell-free assays may be used to demonstrate human c-IAP1/2-specific binding; preferred are rapid in vitro, cell-free assays such as mediating or inhibiting human c-IAP1/2-protein (e.g. human c-IAP1-TRAF2) binding, immunoassays, etc.

The claimed human c-IAP proteins are isolated, partially pure or pure and are typically recombinantly produced. An "isolated" protein for example, is unaccompanied by at least some of the material with which it is associated in its natural state and constitutes at least about 2%, and preferably at least about 5% by weight of the total protein in a given sample; a partially pure protein constitutes at least about 10%, preferably at least about 30%, and more preferably at least about 60% by weight of the total protein in a given sample; and a pure protein constitutes at least about 70%, preferably at least about 90%, and more preferably at least about 95% by weight of the total protein in a given sample. A wide variety of molecular and biochemical methods are available for generating and expressing the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, NY) or that are otherwise known in the art.

The invention provides human c-IAP1/2-specific binding agents including substrates, natural intracellular binding targets, etc. and methods of identifying and making such agents, and their use in diagnosis, therapy and pharmaceutical development. For example, human c-IAP1/2-specific agents are useful in a variety of diagnostic and therapeutic applications, especially where disease or disease prognosis is associated with improper utilization of a pathway involving human c-IAP1/2, e.g. apoptosis. Novel human c-IAP1/2-specific binding agents include human c-IAP1/2-specific antibodies and other natural intracellular binding agents identified with assays such as one- and two-hybrid screens, non-natural intracellular binding agents identified in screens of chemical libraries, etc.

The invention also provides nucleic acids encoding the subject proteins, which nucleic acids may be part of human c-IAP1/2-expression vectors and may be incorporated into recombinant cells for expression and screening, transgenic animals for functional studies (e.g. the efficacy of candidate drugs for disease associated with c-IAP1/2 mediated signal transduction), etc., and nucleic acid hybridization probes and replication/amplification primers having a human c-IAP1/2 cDNA specific sequence contained in SEQUENCE ID NO: 1 or 3. Nucleic acids encoding human c-IAP1/2 are isolated from eukaryotic cells, preferably human cells, by screening cDNA libraries with probes or PCR primers derived from the disclosed human c-IAP1/2 cDNA.

In addition, the invention provides nucleic acids sharing sufficient sequence similarity with that of the disclosed human c-IAP1/2 cDNAs to effect hybridization thereto. Such human c-IAP1/2 cDNA homologs are capable of hybridizing to the human c-IAP1/2-encoding nucleic acid defined by SEQUENCE ID NO: 1 or 3 under stringency conditions characterized by a hybridization buffer comprising 30% formamide in 5 x SSPE (0.18 M NaCl, 0.01 M $NaPO_4$, pH7.7, 0.001 M EDTA) buffer at a temperature of 42° C. and remaining bound when subject to washing at 42° C. with the 0.2 x SSPE. Preferred nucleic acids will hybridize in a hybridization buffer comprising 50% formamide in 5 x SSPE buffer at a temperature of 42 C and remain bound when subject to washing at 42° C. with 0.2 x SSPE buffer at 42° C. Human c-IAP1/2 cDNA homologs can also be characterized by BLASTX (Altschul et al. (1990) Basic Local Alignment Search Tool, J Mol Biol 215,403–410) probability scores. Using this nucleic acid sequence search program BLASTX, complete coding region human c-IAP1/2 cDNA homologs provide a Probability P(N) score of less than 1.0 e-200. More preferred nucleic acids encode c-IAPs with at least about 50%, preferably at least about 60%, more preferably at least 70% pair-wise identity to at least one of SEQUENCE ID NOS: 2 and 4.

The subject nucleic acids are isolated, i.e. constitute at least about 0.5%, preferably at least about 5% by weight of total nucleic acid present in a given fraction. The subject nucleic acids find a wide variety of applications including use as translatable transcripts, hybridization probes, PCR primers, therapeutic nucleic acids, etc.; use in detecting the presence of human c-IAP1/2 genes and gene transcripts, in detecting or amplifying nucleic acids encoding additional human c-IAP1/2 homologs and structural analogs, and in gene therapy applications. When used as expression constructs, the nucleic acids are usually recombinant, meaning they comprise a sequence joined to a nucleotide other than that which it is joined to on a natural chromosome. The subject nucleic acids may be contained within vectors, cells or organisms.

In diagnosis, c-IAP1/2 hybridization probes find use in identifying wild-type and mutant c-IAP1/2 alleles in clinical and laboratory samples. Mutant alleles are used to generate allele-specific oligonucleotide (ASO) probes for high-throughput clinical diagnoses. In therapy, therapeutic c-IAP1/2 nucleic acids are used to modulate cellular expression or intracellular concentration or availability of active c-IAP1/2. A wide variety of indications may be treated, either prophylactically or therapeutically with the subject compositions. For example, where cell-specific apoptosis or other limitation of cell growth is desired, e.g. neoproliferative disease, a reduction in c-IAP1/2 expression is effected by introducing into the targeted cell type c-IAP1/2 nucleic acids which reduce the functional expression of c-IAP1/2 gene products (e.g. nucleic acids capable of inhibiting translation of a c-IAP1/2 protein). Conditions for treatment include restenosis, where vascular smooth muscle cells are involved, inflammatory disease states, where endothelial cells, inflammatory cells and glomerular cells are involved, myocardial infarction, where heart muscle cells are involved, glomerular nephritis, where kidney cells are involved, transplant rejection where endothelial cells are involved, infectious diseases such as HIV infection where certain immune cells and other infected cells are involved, or the like.

These c-IAP1/2 inhibitory nucleic acids are typically antisense: single-stranded sequences comprising complements of the disclosed c-IAP1/2 encoding nucleic acid. Antisense modulation of the expression of a given c-IAP1/2 protein may employ c-IAP1/2 antisense nucleic acids operably linked to gene regulatory sequences. Cell are transfected with a vector comprising a c-IAP1/2 sequence with a promoter sequence oriented such that transcription of the gene yields an antisense transcript capable of binding to endogenous c-IAP1/2 protein encoding MRNA. Transcription of the antisense nucleic acid may be constitutive or inducible and the vector may provide for stable extrachromosomal maintenance or integration. Alternatively, single-stranded antisense nucleic acids that bind to genomic DNA or mRNA encoding a given c-IAP1/2 protein may be administered to the target cell, in or temporarily isolated from a host, at a concentration that results in a substantial reduction in expression of the targeted protein.

In other indications, e.g. certain hypersensitivities, atrophic diseases, etc., a reduction in apoptosis is desired. In these applications, an enhancement in c-IAP1/2 expression is effected by introducing into the targeted cell type c-IAP1/2 nucleic acids which increase the functional expression of c-IAP1/2 gene products. Conditions for treatment include multiple sclerosis, where certain neuronal cells are involved, inflammatory disease states such as rheumatoid arthritis, where bystander cells are involved, transplant rejection where graft cells are involved, infectious diseases such as HIV infection where certain uninfected host cells are involved, or the like. Such nucleic acids may be c-IAP1/2 expression vectors, vectors which upregulate the functional expression of an endogenous c-IAP 1/2 allele, or replacement vectors for targeted correction of c-IAP1/2 mutant alleles.

Various techniques may be employed for introducing of the nucleic acids into viable cells. The techniques vary depending upon whether one is using the subject compositions in culture or in vivo in a host. Various techniques which have been found efficient include transfection with a retrovirus, viral coat protein-liposome mediated transfection, see Dzau et al., *Trends in Biotech* 11, 205–210 (1993). In some situations it is desirable to provide the nucleic acid source with an agent which targets the target cells, such as an antibody specific for a surface membrane protein on the target cell, a ligand for a receptor on the target cell, etc. Where liposomes are employed, proteins which bind to a surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. In liposomes, the nucleic acid concentration in the lumen will generally be in the range of about 0.01 $\mu$M to 10 $\mu$M. For other techniques, the concentration and application rate is determined empirically, using conventional techniques to determine desired ranges.

Application of the subject therapeutics may be systemic or local, i.e. administered at the site of interest. Various techniques can be used for providing the subject compositions at the site of interest, such as injection, use of catheters, trocars, projectiles, pluronic gel, stents, sustained drug release polymers or other device which provides for internal access. Where an organ or tissue is accessible because of removal from the patient, such organ or tissue may be bathed in a medium containing the subject compositions, the subject compositions may be painted onto the organ, or may be applied in any convenient way. Systemic administration of the nucleic acid may be effected using naked DNA, lipofection, liposomes with tissue targeting (e.g. antibody).

The invention provides methods and compositions for enhancing the yield of many recombinantly produced proteins, such as tissue plasminogen activator (t-PA), by increasing maximum cell densities and survival time of host production cells in culture. Specifically, cultured cells are transfected with nucleic acids which effect the up-regulation of endogenous c-IAP or the expression of an exogenous c-IAP. For example, nucleic acids encoding functional c-IAP operably linked to a transcriptional promoter are used to over-express the exogenous c-IAP in the host cell (see, experimental section, below). Such transformed cells demonstrate enhanced survival ability at elevated cell densities and over extended culture periods.

The invention provides efficient methods of identifying pharmacological agents or lead compounds for agents active at the level of a human c-IAP1/2 modulatable cellular function, particularly human c-IAP1/2 mediated signal transduction, especially in apoptosis. Generally, these screening methods involve assaying for compounds which modulate a human c-IAP1/2 interaction with a natural c-IAP1/2 binding target. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development. Target indications may include infection, genetic disease, cell growth and regulatory disfunction, such as neoplasia, inflammation, hypersensitivity, etc.

A wide variety of assays for binding agents are provided including protein-protein binding assays, immunoassays, cell based assays, etc. The human c-IAP1/2 compositions used the methods are usually added in an isolated, partially pure or pure form and are typically recombinantly produced. The human c-IAP1/2 may be part of a fusion product with another peptide or polypeptide, e.g. a polypeptide that is capable of providing or enhancing protein-protein binding, stability under assay conditions (e.g. a tag for detection or anchoring), etc. The assay mixtures comprise a natural intracellular human c-IAP1/2 binding target such as a TRAF. While native binding targets may be used, it is frequently preferred to use portions (e.g. peptides, nucleic acid fragments) thereof so long as the portion provides binding affinity and avidity to the subject human c-IAP1/2 conveniently measurable in the assay. The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like salts, buffers, neutral proteins, e.g. albumin, detergents, etc. which may be used to facilitate optimal binding and/or reduce non-specific or background interactions, etc. Also, reagents that otherwise improve the efficiency of the assay, such as protease inhibitors, nuclease inhibitors, antimicrobial agents, etc. may be used.

The resultant mixture is incubated under conditions whereby, but for the presence of the candidate pharmacological agent, the human c-IAP1/2 specifically binds the cellular binding target, portion or analog with a reference binding affinity. The mixture components can be added in any order that provides for the requisite bindings. Incubations may be performed at any temperature which facilitates optimal binding, typically between 4 and 40° C., more commonly between 15° and 40° C. Incubation periods are likewise selected for optimal binding but also minimized to facilitate rapid, high-throughput screening, and are typically between 0.1 and 10 hours, preferably less than 5 hours, more preferably less than 2 hours.

After incubation, the agent-influenced binding between the human c-IAP1/2 and one or more binding targets is detected by any convenient way. For cell-free binding type assays, a separation step is often used to separate bound from unbound components. Separation may be effected by precipitation (e.g. TCA precipitation, immunoprecipitation, etc.), immobilization (e.g on a solid substrate), etc., followed by washing by, for examples, membrane filtration (e.g. Whatman's P-81 ion exchange paper, Polyfiltronic's hydrophobic GFC membrane, etc.), gel chromatography (e.g. gel filtration, affinity, etc.). In addition, one of the components usually comprises or is coupled to a label. A wide variety of labels may be employed - essentially any label that provides for detection of bound protein. The label may provide for direct detection as radioactivity, luminescence, optical or electron density, etc. or indirect detection such as an epitope tag, an enzyme, etc. A variety of methods may be used to detect the label depending on the nature of the label and other assay components. For example, the label may be detected bound to the solid substrate or a portion of the bound complex containing the label may be separated from the solid substrate, and thereafter the label detected. Labels may be directly detected through optical or electron density, radiative emissions, nonradiative energy transfers, etc. or indirectly detected with antibody conjugates, etc. For example, in the case of radioactive labels, emissions may be detected directly, e.g. with particle counters or indirectly, e.g. with scintillation cocktails and counters.

The following experiments and examples are offered by way of illustration and not by way of limitation.

EXPERIMENTAL

The murine cellular inhibitor of apoptosis protein 1 (c-IAP1) was biochemically purified as a TNF-R2 associated protein using coimmunoprecipitation Rothe et al. (1994) supra. A large scale protein purification protocol provided material sufficient for peptide sequencing. Fully degenerate oligonucleotides corresponding to two of the isolated peptides were used to specifically amplify a 0.75 kb DNA fragment from mouse CT6 RNA by Reverse Transcription-PCR. This DNA fragment was used to isolate full-length cDNA clones from a mouse CT6 cDNA library by hybridization (50% formamide, 5xSSPE, 42° C.; filters washed at 42° C. with 0.2XSSPE, where 1xSSPE is 0.18 M NaCl, 0.01 M NaPO$_4$, pH7.7, 0.001 M EDTA).

DNA sequence analysis predicted an open reading frame encoding a 612 amino acid protein that shows significant sequence similarity (36% amino acid identity) with the 'inhibitor of apoptosis protein' (IAP) from insect viruses (Clem, R. J. and Miller, L. K., 1994, supra) and the human 'neuronal apoptosis inhibitory protein' (NAIP) (23% amino acid identity), that is involved in spinal muscular atrophy (SMA) an inherited disease in humans (Roy et., 1995, supra). To obtain the human c-IAP1 gene, the originally amplified mouse DNA fragment was used as a probe to screen a HeLa cDNA library (30% formamide, 5xSSPE, 42° C.; filters washed at 42° C. with 0.2xSSPE). Sequence analysis of the isolated cDNA clones revealed that they correspond to two distinct genes, designated c-IAP1 and c-IAP2. The human c-IAP1 cDNA encodes a protein of 618 amino acids that is 84% identical to murine c-IAP1. The human c-IAP2 cDNA encodes a protein of 604 amino acids that shares a high degree of amino acid identity with both murine and human c-IAP1 (72% and 73%, respectively) and represents another member of the IAP superfamily.

Comparison of the amino acid sequence of members of the IAP superfamily reveals that they are comprised of at least three distinct domains. The N-terminal region of all IAP family members is comprised of 'baculovirus IAP repeat' (BIR) motifs (Birnbaum et al., 1994, supra). While the viral proteins contain two repeats, the mammalian homologs (c-IAP1, -2) possess three BIR motifs. Similarly, NAIP contains three BIR repeats. In addition to BIR motifs viral IAPs contain a C-terminal RING finger motif. This Zn-binding domain is also present in c-IAP1 and -2 but not in NAIP. Thus c-IAP1 and -2 define a distinct subfamily within the IAP superfamily that contain three BIR motifs and a RING finger motif. A RING finger domain is also present at the N-terminus of TRAF2 and has been shown to be involved in TRAF2 signal transduction. The RING finger motifs of c-IAP1 and -2 share significant sequence homology with the RING finger domains of viral IAPs but no homology with the TRAF2 RING finger domain besides the conserved cysteine and histidine residues. The region between the BIR domain and the RING finger domain of c-IAP1 and -2 is strongly conserved but does not reveal any significant homology to other members of the IAP family or any other proteins in the NCBI database.

A yeast two-hybrid system was used to determine how c-IAP1 and -2 interact with TNF-R2 and/or TRAFs. The following results were obtained indistinguishably for c-IAP1 and c-IAP2. Two-hybrid analysis revealed that c-IAP1 does not directly interact with TNF-12. However, a direct interaction could be detected between c-IAP1 and TRAF2. The conserved TRAF domain of TRAF2 (amino acids 264–501) is sufficient to mediate this interaction. Consistently, c-IAP1 also interacted with TRAF1. Further analysis demonstrated that the coiled-coil region within the TRAF domain of TRAF2 (amino acids 251-358) is required for interaction with c-IAP1. In contrast, the C-terminal region of the TRAF domain (amino acids 359–501) that mediates the association of TNF-R2 with TRAF2 is dispensable for interaction of c-IAP1 with TRAF2. Thus c-IAP1 and TNF-R2 bind to non-overlapping docking sites within the TRAF domain of TRAF2. Consistently, c-IAP1 does not interact with TRAF3 (e.g. Cheng et al. (1995), supra), which does not contain a coiled-coil region with sequence similarity to TRAF2 1RAF1. Deletion mutagenesis of c-IAP1 indicated that the N-terminal half of the protein containing the three BIR motifs (amino acids 1–336 of c-IAP1 and 1–396 of c-IAP2) is sufficient for interaction with TRAF2 and TRAFl. Similarly, combinations of two of the three BIR motifs e.g. amino acid residues 46–99 and 204–249 of c-IAP1 and 29–82 and 189–234 of c-IAP2, separated by IAP1 derived intervening sequences of varying lengths are assayed for TRAFI and TRAF2 binding. This indicates that BIR motifs represent a novel protein:protein interaction domain. The RING finger domain of c-IAP1/2 (amino acids 571–618 of c-IAP1 and 557–604 of c-IAP2) is not required for interaction with TRAFs, but rather mediates subsequent steps in the c-IAP1/2 signaling cascade. Similarly, a variety of c-IAP1 derived N-termninal leader sequences fused to the c-IAP1 RING finger domain are used to assay signal transduction mediation. In an analogous situation, the RING finger domain of TRAF2 has been demonstrated to be required for TRAF2-mediated activation of NF-κB.

A transfection based co-immunoprecipitation assay was used to investigate how c-IAP1 interacts with the complex of TNF-R2 and TRAFs. In this system c-IAP1 was N-terminally tagged with a FLAG epitope peptide and expressed in human embryonic 293 cells under the control of a constitutive CMV promotor (pRK vector). The c-IAP1 expression vector was transiently co-transfected into 293 cells with expression vectors for TNF-R2 and TRAFs. After 24–36 h, the cells were harvested and extracts immunoprecipitated with anti-TNF-R2 antibodies, followed by Western analysis with anti-FLAG antibodies. This assay demonstrated that while c-IAP1 associates directly with TRAF1 and TRAF2, its interaction with TNF-R2 is indirect and requires the heterocomplex of TRAFP and TRAF2. Thus, c-IAP1 is a component of the TNF-R2 (CD40)/TRAF signaling complex.

To determine the functional properties of c-IAP1 transient transfection assays were performed in human rhabdomyosarcoma KYM1 cells. The results indicate that overexpression of c-IAP1 but not of control vector, TRAFI or TRAF2 protects KYML cells from TNF-induced programmed cell death (apoptosis). Hence, c-IAP1 regulates the cellular response to TNF by modulating TNF responsiveness, e.g. the initiation of an apoptotic or protective program. The transient transfection assay also finds use as a drug screening assay. In this application, candidate agents are screened as above for their ability to modulate the ability of c-IAP1 to downregulate apoptosis.

EXAMPLES

1. Protocol for human c-IAP1 - TRAF2 binding assay.

A. Reagents:

Neutralite Avidin: 20 $\mu$g/ml in PBS.

Blocking buffer: 5% BSA, 0.5% Tween 20 in PBS; 1 hour at room temperature.

Assay Buffer: 100 mM KCl, 20 mM HEPES pH 7.6, 0.25 mM EDTA, 1% glycerol, 0.5% NP-40, 50 mM β-mercaptoethanol, 1 mg/ml BSA, cocktail of protease inhibitors.

$^{33}$P human c-IAP1 10x stock: $10^{-8}$–$10^{-6}$ M unlabeled human c-IAP1 supplemented with 200,000–250,000 cpm of labeled human c-IAP1/21 (Beckman counter). Place in the 4° C. microfridge during screening.

Protease inhibitor cocktail (1000X): 10 mg Trypsin Inhibitor (BMB # 109894), 10 mg Aprotinin (BMB # 236624), 25 mg Benzamidine (Sigma # B-6506), 25 mg Leupeptin (BMB # 1017128), 10 mg APMSF (BMB # 917575), and 2mM NaVo$_3$ (Sigma # S-6508) in 10 ml of PBS.

TRAF2: $10^{-8}$–$10^{-5}$ M biotinylated truncated TRAF2 (residues 264–501) in PBS.

B. Preparation of assay plates:

Coat with 120 1 of stock N-Avidin per well overnight at 4° C.

Wash 2 times with 200 $\mu$l PBS.

Block with 150 ||l of blocking buffer.

Wash 2 times with 200 $\mu$l PBS.

C. Assay:

Add 40 $\mu$l assay buffer/well.

Add 10 $\mu$l compound or extract.

Add 10 $\mu$l $^{33}$P-human c-IAP1 (20,000–25,000 cpm/ 0.1–10 pmoles/well=$10^{-9}$–$10^{-7}$ M final concentration).

Shake at 25° C. for 15 minutes.

Incubate additional 45 minutes at 25° C.

Add 40 $\mu$l biotinylated truncated TRAF2 (0.1–10 pmoles/ 40 $\mu$l in assay buffer)

Incubate 1 hour at room temperature.

Stop the reaction by washing 4 times with 200 $\mu$l PBS.

Add 150 $\mu$l scintillation cocktail.

Count in Topcount.

D. Controls for all assays (located on each plate):
   a. Non-specific binding
   b. Soluble (non-biotinylated truncated TRAF2) at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

| | | |
|---|---|---|
| SEQUENCE ID NO: 1, 2 | h (human) c-IAP1 | cDNA, protein |
| SEQUENCE ID NO: 3, 4 | h c-IAP2 | cDNA, protein |
| SEQUENCE ID NO: 5, 6 | h c-IAP1,2 repeat 1 | protein, protein |
| SEQUENCE ID NO: 7, 8 | h c-IAP1,2 repeat 2 | protein, protein |
| SEQUENCE ID NO: 9, 10 | h c-IAP1,2 repeat 3 | protein, protein |
| SEQUENCE ID NO: 11, 12 | h c-IAP1,2 RING finger | protein, protein |
| SEQUENCE ID NO: 13, 14 | m (murine) c-IAP | cDNA, protein |

What is claimed is:

1. An isolated nucleic acid comprising the sequence set forth by nucleotides 1053–1196 of SEQ ID NO: 1.

2. A method of inhibiting TNF-mediated apoptosis in a cell comprising the step of introducing into said cell a nucleic acid according to claim 1 whereby said nucleic acid is expressed in said cell and the resultant gene product promotes or inhibits TNF-mediated apoptosis in said cell, wherein said method is performed in vitro.

3. The isolated nucleic acid of claim 1, wherein said nucleic acid comprises SEQ ID NO:1.

4. An isolated nucleic acid comprising the sequence set forth by SEQ ID NO: 3.

5. A method of inhibiting TNF-mediated apoptosis in a cell comprising the step of introducing into said cell a nucleic acid according to claim 4 whereby said nucleic acid is expressed in said cell and the resultant gene product promotes or inhibits TNF-mediated apoptosis in said cell, wherein said method is performed in vitro.

6. An isolated nucleic acid encoding a human cellular inhibitor of apoptosis protein (c-IAP) comprising the sequence set forth by residues 287–334 of SEQ ID NO: 2.

7. The isolated nucleic acid according to claim 6 encoding a human cellular inhibitor of apoptosis protein (c-IAP) comprising SEQ ID NO:2.

8. A method of making a human cellular inhibitor of apoptosis protein (c-IAP) comprising introducing a nucleic acid according to claim 6 into a host cell, growing said host cell under conditions whereby said nucleic acid is expressed as a transcript and said transcript is expressed as a translation product comprising a cellular inhibitor of apoptosis protein, and isolating said translation product.

9. A method of screening for compounds which potentially modulate a human c-IAP interaction with a natural c-IAP binding target, said method comprising the steps of:
   incubating a mixture comprising:
      a human c-IAP made by a method according to claim 8,
      a natural intracellular human c-IAP binding target, wherein said binding target is capable of specifically binding said human c-IAP, and
      a candidate agent;
   under conditions whereby, but for the presence of said candidate agent, said human c-IAP specifically binds said binding target at a reference affinity;
   detecting the binding affinity of said human c-IAP to said binding target to determine an agent-biased affinity,
   wherein a difference between the agent-biased affinity and the test affinity indicates that said candidate agent modulates a human c-IAP interaction with a natural c-IAP binding target.

10. A method according to claim 9, wherein said human c-IAP binding target comprises a TRAF or fragment thereof sufficient to provide for c-IAP-specific binding.

11. A method of inhibiting TNF-mediated apoptosis in a cell comprising the step of introducing into said cell a nucleic acid according to claim 6 whereby said nucleic acid is expressed in said cell and the resultant gene product promotes or inhibits apoptosis in said cell, wherein said method is performed in vitro.

12. An isolated nucleic acid encoding a human cellular inhibitor of apoptosis protein (c-IAP) comprising the sequence set forth by SEQ ID NO: 4.

13. An isolated nucleic acid encoding a human cellular inhibitor of apoptosis protein (c-IAP) comprising at least two of: a first domain comprising SEQ ID NO: 5 or 6, a second domain comprising SEQ ID NO: 7 or 8, and a third domain comprising SEQ ID NO: 9 or 10.

14. A method of making a human cellular inhibitor of apoptosis protein (c-IAP) comprising introducing a nucleic acid according to claim 13 into a host cell, growing said host cell under conditions whereby said nucleic acid is expressed as a transcript and said transcript is expressed as a translation product comprising a cellular inhibitor of apoptosis protein, and isolating said translation product.

15. A method of screening for compounds which potentially modulate a human c-IAP interaction with a natural c-IAP binding target, said method comprising the steps of:
   incubating a mixture comprising:
      a human c-IAP made by a method according to claim 14,
      a natural intracellular human c-IAP binding target, wherein said binding target is capable of specifically binding said human c-IAP, and
      a candidate agent;
   under conditions whereby, but for the presence of said candidate agent, said human c-IAP specifically binds said binding target at a reference affinity;
   detecting the binding affinity of said human c-IAP to said binding target to determine an agent-biased affinity,
   wherein a difference between the agent-biased affinity and the test affinity indicates that said candidate agent modulates a human c-IAP interaction wit a natural c-IAP binding target.

16. A method according to claim 15, wherein said human c-IAP binding target comprises a TRAF or fragment thereof sufficient to provide for c-IAP-specific binding.

17. A method of inhibiting TNF-mediated apoptosis in a cell comprising the step of introducing into said cell a nucleic acid according to claim 13 whereby said nucleic acid is expressed in said cell and the resultant gene product promotes or inhibits apoptosis in said cell, wherein said method is performed in vitro.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
         (A) LENGTH: 2589 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:1:

-continued

```
TCTAAGTAGT ATCTTGGAAA TTCAGAGAGA TACTCATCCT ACCTGAATAT AAACTGAGAT      60
AAATCCAGTA AAGAAAGTGT AGTAAATTCT ACATAAGAGT CTATCATTGA TTTCTTTTGG     120
TGGTAAAAAT CTTAGTTCAT GTGAAGAAAT TCATGTGAA TGTTTTAGCT ATCAAACAGC      180
ACTGTCACCT ACTCATGCAC AAAACTGCCT CCCAAAGACT TTTCCCAGGT CCCTCGTATC     240
AAAACATTAA GAGTATAATG GAAGATAGCA CGATCTTGTC AGATTGGACA AACAGCAACA     300
AACAAAAAAT GAAGTATGAC TTTTCCTGTG AACTCTACAG AATGTCTACA TATTCAACTT     360
TCCCCGCCGG GGTGCCTGTC TCAGAAAGGA GTCTTGCTCG TGCTGGTTTT TATTATACTG     420
GTGTGAATGA CAAGGTCAAA TGCTTCTGTT GTGGCCTGAT GCTGGATAAC TGGAAACTAG     480
GAGACAGTCC TATTCAAAAG CATAAACAGC TATATCCTAG CTGTAGCTTT ATTCAGAATC     540
TGGTTTCAGC TAGTCTGGGA TCCACCTCTA AGAATACGTC TCCAATGAGA AACAGTTTTG     600
CACATTCATT ATCTCCCACC TTGGAACATA GTAGCTTGTT CAGTGGTTCT TACTCCAGCC     660
TTTCTCCAAA CCCTCTTAAT TCTAGAGCAG TTGAAGACAT CTCTTCATCG AGGACTAACC     720
CCTACAGTTA TGCAATGAGT ACTGAAGAAG CCAGATTTCT TACCTACCAT ATGTGGCCAT     780
TAACTTTTTT GTCACCATCA GAATTGGCAA GAGCTGGTTT TTATTATATA GGACCTGGAG     840
ATAGGGTAGC CTGCTTTGCC TGTGGTGGGA AGCTCAGTAA CTGGGAACCA AAGGATGATG     900
CTATGTCAGA ACACCGGAGG CATTTTCCCA ACTGTCCATT TTTGGAAAAT TCTCTAGAAA     960
CTCTGAGGTT TAGCATTTCA AATCTGAGCA TGCAGACACA TGCAGCTCGA ATGAGAACAT    1020
TTATGTACTG GCCATCTAGT GTTCCAGTTC AGCCTGAGCA GCTTGCAAGT GCTGGTTTTT    1080
ATTATGTGGG TCGCAATGAT GATGTCAAAT GCTTTTGTTG TGATGGTGGC TTGAGGTGTT    1140
GGGAATCTGG AGATGATCCA TGGGTAGAAC ATGCCAAGTG GTTTCCAAGG TGTGAGTTCT    1200
TGATACGAAT GAAAGGCCAA GAGTTTGTTG ATGAGATTCA AGGTAGATAT CCTCATCTTC    1260
TTGAACAGCT GTTGTCAACT TCAGATACCA CTGGAGAAGA AAATGCTGAC CCACCAATTA    1320
TTCATTTTGG ACCTGGAGAA AGTTCTTCAG AAGATGCTGT CATGATGAAT ACACCTGTGG    1380
TTAAATCTGC CTTGGAAATG GGCTTTAATA GAGACCTGGT GAAACAAACA GTTCAAAGTA    1440
AAATCCTGAC AACTGGAGAG AACTATAAAA CAGTTAATGA TATTGTGTCA GCACTTCTAA    1500
ATGCTGAAGA TGAAAAAAGA GAGGAGGAGA AGGAAAAACA AGCTGAAGAA ATGGCATCAG    1560
ATGATTTGTC ATTAATTCGG AAGAACAGAA TGGCTCTCTT TCAACAATTG ACATGTGTGC    1620
TTCCTATCCT GGATAATCTT TTAAAGGCCA ATGTAATTAA TAAACAGGAA CATGATATTA    1680
TTAAACAAAA AACACAGATA CCTTTACAAG CGAGAGAACT GATTGATACC ATTTTGGTTA    1740
AAGGAAATGC TGCGGCCAAC ATCTTCAAAA ACTGTCTAAA AGAAATTGAC TCTACATTGT    1800
ATAAGAACTT ATTTGTGGAT AAGAATATGA AGTATATTCC AACAGAAGAT GTTTCAGGTC    1860
TGTCACTGGA AGAACAATTG AGGAGGTTGC AAGAAGAACG AACTTGTAAA GTGTGTATGG    1920
ACAAAGAAGT TTCTGTTGTA TTTATTCCTT GTGGTCATCT GGTAGTATGC AGGAATGTG    1980
CCCCTTCTCT AAGAAAATGC CCTATTTGCA GGGGTATAAT CAAGGGTACT GTTCGTACAT    2040
TTCTCTCTTA AAGAAAAATA GTCTATATTT TAACCTGCAT AAAAAGGTCT TTAAAATATT    2100
GTTGAACACT TGAAGCCATC TAAAGTAAAA AGGGAATTAT GAGTTTTTCA ATTAGTAACA    2160
TTCATGTTCT AGTCTGCTTT GGTACTAATA ATCTTGTTTC TGAAAAGATG GTATCATATA    2220
TTTAATCTTA ATCTGTTTAT TTACAAGGGA AGATTTATGT TTGGTGAACT ATATTAGTAT    2280
GTATGTGTAC CTAAGGGAGT AGTGTCACTG CTTGTTATGC ATCATTTCAG GAGTTACTGG    2340
```

```
ATTTGTTGTT CTTTCAGAAA GCTTTGAATA CTAAATTATA GTGTAGAAAA GAACTGGAAA    2400

CCAGGAACTC TGGAGTTCAT CAGAGTTATG GTGCCGAATT GTCTTTGGTG CTTTTCACTT    2460

GTGTTTTAAA ATAAGGATTT TTCTCTTATT TCTCCCCCTA GTTTGTGAGA AACATCTCAA    2520

TAAAGTGCTT TAAAAAAAAA AAAAAAAAAA AAAAAAAAAA AAAAAAAAAA AAAAAAAAAA    2580

AAAAAAAAA                                                             2589
```

(2) INFORMATION FOR SEQ ID NO:2:

(i) SEQUENCE CHARACTERISTICS:
        (A) LENGTH: 618 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met His Lys Thr Ala Ser Gln Arg Leu Phe Pro Gly Pro Ser Tyr Gln
  1               5                  10                  15

Asn Ile Lys Ser Ile Met Glu Asp Ser Thr Ile Leu Ser Asp Trp Thr
             20                  25                  30

Asn Ser Asn Lys Gln Lys Met Lys Tyr Asp Phe Ser Cys Glu Leu Tyr
         35                  40                  45

Arg Met Ser Thr Tyr Ser Thr Phe Pro Ala Gly Val Pro Val Ser Glu
     50                  55                  60

Arg Ser Leu Ala Arg Ala Gly Phe Tyr Tyr Thr Gly Val Asn Asp Lys
 65                  70                  75                  80

Val Lys Cys Phe Cys Cys Gly Leu Met Leu Asp Asn Trp Lys Leu Gly
                 85                  90                  95

Asp Ser Pro Ile Gln Lys His Lys Gln Leu Tyr Pro Ser Cys Ser Phe
                100                 105                 110

Ile Gln Asn Leu Val Ser Ala Ser Leu Gly Ser Thr Ser Lys Asn Thr
            115                 120                 125

Ser Pro Met Arg Asn Ser Phe Ala His Ser Leu Ser Pro Thr Leu Glu
        130                 135                 140

His Ser Ser Leu Phe Ser Gly Ser Tyr Ser Ser Leu Ser Pro Asn Pro
145                 150                 155                 160

Leu Asn Ser Arg Ala Val Glu Asp Ile Ser Ser Ser Arg Thr Asn Pro
                165                 170                 175

Tyr Ser Tyr Ala Met Ser Thr Glu Glu Ala Arg Phe Leu Thr Tyr His
            180                 185                 190

Met Trp Pro Leu Thr Phe Leu Ser Pro Ser Glu Leu Ala Arg Ala Gly
        195                 200                 205

Phe Tyr Tyr Ile Gly Pro Gly Asp Arg Val Ala Cys Phe Ala Cys Gly
    210                 215                 220

Gly Lys Leu Ser Asn Trp Glu Pro Lys Asp Asp Ala Met Ser Glu His
225                 230                 235                 240

Arg Arg His Phe Pro Asn Cys Pro Phe Leu Glu Asn Ser Leu Glu Thr
                245                 250                 255

Leu Arg Phe Ser Ile Ser Asn Leu Ser Met Gln Thr His Ala Ala Arg
            260                 265                 270

Met Arg Thr Phe Met Tyr Trp Pro Ser Ser Val Pro Val Gln Pro Glu
        275                 280                 285

Gln Leu Ala Ser Ala Gly Phe Tyr Tyr Val Gly Arg Asn Asp Asp Val
    290                 295                 300
```

-continued

```
Lys Cys Phe Cys Cys Asp Gly Gly Leu Arg Cys Trp Glu Ser Gly Asp
305                 310                 315                 320

Asp Pro Trp Val Glu His Ala Lys Trp Phe Pro Arg Cys Glu Phe Leu
                325                 330                 335

Ile Arg Met Lys Gly Gln Glu Phe Val Asp Glu Ile Gln Gly Arg Tyr
                340                 345                 350

Pro His Leu Leu Glu Gln Leu Leu Ser Thr Ser Asp Thr Thr Gly Glu
                355                 360                 365

Glu Asn Ala Asp Pro Pro Ile Ile His Phe Gly Pro Gly Glu Ser Ser
370                 375                 380

Ser Glu Asp Ala Val Met Met Asn Thr Pro Val Val Lys Ser Ala Leu
385                 390                 395                 400

Glu Met Gly Phe Asn Arg Asp Leu Val Lys Gln Thr Val Gln Ser Lys
                405                 410                 415

Ile Leu Thr Thr Gly Glu Asn Tyr Lys Thr Val Asn Asp Ile Val Ser
                420                 425                 430

Ala Leu Leu Asn Ala Glu Asp Glu Lys Arg Glu Glu Lys Glu Lys
                435                 440                 445

Gln Ala Glu Glu Met Ala Ser Asp Asp Leu Ser Leu Ile Arg Lys Asn
450                 455                 460

Arg Met Ala Leu Phe Gln Gln Leu Thr Cys Val Leu Pro Ile Leu Asp
465                 470                 475                 480

Asn Leu Leu Lys Ala Asn Val Ile Asn Lys Gln Glu His Asp Ile Ile
                485                 490                 495

Lys Gln Lys Thr Gln Ile Pro Leu Gln Ala Arg Glu Leu Ile Asp Thr
                500                 505                 510

Ile Leu Val Lys Gly Asn Ala Ala Asn Ile Phe Lys Asn Cys Leu
                515                 520                 525

Lys Glu Ile Asp Ser Thr Leu Tyr Lys Asn Leu Phe Val Asp Lys Asn
                530                 535                 540

Met Lys Tyr Ile Pro Thr Glu Asp Val Ser Gly Leu Ser Leu Glu Glu
545                 550                 555                 560

Gln Leu Arg Arg Leu Gln Glu Glu Arg Thr Cys Lys Val Cys Met Asp
                565                 570                 575

Lys Glu Val Ser Val Val Phe Ile Pro Cys Gly His Leu Val Val Cys
                580                 585                 590

Gln Glu Cys Ala Pro Ser Leu Arg Lys Cys Pro Ile Cys Arg Gly Ile
                595                 600                 605

Ile Lys Gly Thr Val Arg Thr Phe Leu Ser
610                 615
```

(2) INFORMATION FOR SEQ ID NO:3:

(i) SEQUENCE CHARACTERISTICS:
        (A) LENGTH: 2601 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
GGGCAGCAGG TTTACAAAGG AGGAAAACGA CTTCTTCTAG ATTTTTTTTT CAGTTTCTTC    60

TATAAATCAA AACTACCTCC CTAGAGAAAG GCTAGTCCCT TTTCTTCCCC ATTCATTTCA   120

TTATGAACAT AGTAGAAAAC AGCATATTCT TATCAAATTT GATGAAAAGC GCCAACACGT   180
```

-continued

```
TTGAACTGAA ATACGACTTG TCATGTGAAC TGTACCGAAT GTCTACGTAT TCCACTTTTC      240

CTGCTGGGGT CCCTGTCTCA GAAAGGAGTC TTGCTCGCGC TGGTTTCTAT TACACTGGTG      300

TGAATGACAA GGTCAAATGC TTCTGTTGTG GCCTGATGCT GGATAACTGG AAAAGAGGAG      360

ACAGTCCTAC TGAAAAGCAT AAAAAGTTGT ATCCTAGCTG CAGATTCGTT CAGAGTCTAA      420

ATTCCGTTAA CAACTTGGAA GCTACCTCTC AGCCTACTTT TCCTTCTTCA GTAACAAATT      480

CCACACACTC ATTACTTCCG GGTACAGAAA ACAGTGGATA TTTCCGTGGC TCTTATTCAA      540

ACTCTCCATC AAATCCTGTA AACTCCAGAG CAAATCAAGA TTTTTCTGCC TTGATGAGAA      600

GTTCCTACCA CTGTGCAATG AATAACGAAA ATGCCAGATT ACTTACTTTT CAGACATGGC      660

CATTGACTTT TCTGTCGCCA ACAGATCTGG CAAAAGCAGG CTTTTACTAC ATAGGACCTG      720

GAGACAGAGT GGCTTGCTTT GCCTGTGGTG GAAAATTGAG CAATTGGGAA CCGAAGGATA      780

ATGCTATGTC AGAACACCTG AGACATTTTC CCAAATGCCC ATTTATAGAA AATCAGCTTC      840

AAGACACTTC AAGATACACA GTTTCTAATC TGAGCATGCA GACACATGCA GCCCGCTTTA      900

AAACATTCTT TAACTGGCCC TCTAGTGTTC TAGTTAATCC TGAGCAGCTT GCAAGTGCGG      960

GTTTTTATTA TGTGGGTAAC AGTGATGATG TCAAATGCTT TTGCTGTGAT GGTGGACTCA     1020

GGTGTTGGGA ATCGGAGAT GATCCATGGG TTCAACATGC CAAGTGGTTT CCAAGGTGTG     1080

AGTACTTGAT AAGAATTAAA GGACAGGAGT TCATCCGTCA AGTTCAAGCC AGTTACCCTC     1140

ATCTACTTGA ACAGCTGCTA TCCACATCAG ACAGCCCAGG AGATGAAAAT GCAGAGTCAT     1200

CAATTATCCA TTTTGAACCT GGAGAAGACC ATTCAGAAGA TGCAATCATG ATGAATACTC     1260

CTGTGATTAA TGCTGCCGTG GAAATGGGCT TTAGTAGAAG CCTGGTAAAA CAGACAGTTC     1320

AGAGAAAAAT CCTAGCAACT GGAGAGAATT ATAGACTAGT CAATGATCTT GTGTTAGACT     1380

TACTCAATGC AGAAGATGAA ATAAGGGAAG AGGAGAGAGA AAGAGCAACT GAGGAAAAAG     1440

AATCAAATGA TTTATTATTA ATCCGGAAGA ATAGAATGGC ACTTTTTCAA CATTTGACTT     1500

GTGTAATTCC AATCCTGGAT AGTCTACTAA CTGCCGGAAT TATTAATGAA CAAGAACATG     1560

ATGTTATTAA ACAGAAGACA CAGACGTCTT TACAAGCAAG AGAACTGATT GATACGATTT     1620

TAGTAAAAGG AAATATTGCA GCCACTGTAT TCAGAAACTC TCTGCAAGAA GCTGAAGCTG     1680

TGTTATATGA GCATTTATTT GTGCAACAGG ACATAAAATA TATTCCCACA GAAGATGTTT     1740

CAGATCTACC AGTGGAAGAA CAATTGCGGA GACTACAAGA AGAAAGAACA TGTAAAGTGT     1800

GTATGGACAA AGAAGTGTCC ATAGTGTTTA TTCCTTGTGG TCATCTAGTA GTATGCAAAG     1860

ATTGTGCTCC TTCTTTAAGA AAGTGTCCTA TTTGTAGGAG TACAATCAAG GGTACAGTTC     1920

GTACATTTCT TCATGAAGA AGAACCAAAA CATCATCTAA ACTTTAGAAT TAATTTATTA     1980

AATGTATTAT AACTTTAACT TTCATCCTAA TTTGGTTTCC TTAAAATTTT TATTTATTTA     2040

CAACTCAACA AACATTGTTT TGTGTAACAT ATTTAATATA TGTATCTAAA CCATATGAAC     2100

ATATATTTTT TAGAAACTAA GAGAATGATA GGCTTTTGTT CTTATGAACG AAAAAGAGGT     2160

AGCACTACAA ACACAATATT CAATCAAAAT TTCAGCATTA TTGAAATTGT AAGTGAAGTA     2220

AAACTTAAGA TATTTGAGTT AACCTTTAAG AATTTTAAAT ATTTTGGCAT TGTACTAATA     2280

CCGGGAACAT GAAGCCAGGT GTGGTGGTAT GTGCCTGTAG TCCCAGGCTG AGGCAAGAGA     2340

ATTACTTGAG CCCAGGAGTT TGAATCCATC CTGGGCAGCA TACTGAGACC CTGCCTTTAA     2400

AAACAAACAG AACAAAAACA AAACACCAGG GACACATTTC TCTGTCTTTT TTGATCAGTG     2460

TCCTATACAT CGAAGGTGTG CATATATGTT GAATGACATT TTAGGGACAT GGTGTTTTA     2520
```

TAAAGAATTC TGTGAGAAAA AATTTAATAA AACCCCCCAA ATTAAAAAAA AAAAAAAAAA    2580

AAAAAAAAAA AAAAAAAAAA A                                             2601

(2) INFORMATION FOR SEQ ID NO:4:

(i) SEQUENCE CHARACTERISTICS:
        (A) LENGTH: 604 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Met Asn Ile Val Glu Asn Ser Ile Phe Leu Ser Asn Leu Met Lys Ser
1               5                   10                  15

Ala Asn Thr Phe Glu Leu Lys Tyr Asp Leu Ser Cys Glu Leu Tyr Arg
            20                  25                  30

Met Ser Thr Tyr Ser Thr Phe Pro Ala Gly Val Pro Val Ser Glu Arg
        35                  40                  45

Ser Leu Ala Arg Ala Gly Phe Tyr Tyr Thr Gly Val Asn Asp Lys Val
    50                  55                  60

Lys Cys Phe Cys Cys Gly Leu Met Leu Asp Asn Trp Lys Arg Gly Asp
65                  70                  75                  80

Ser Pro Thr Glu Lys His Lys Lys Leu Tyr Pro Ser Cys Arg Phe Val
                85                  90                  95

Gln Ser Leu Asn Ser Val Asn Asn Leu Glu Ala Thr Ser Gln Pro Thr
            100                 105                 110

Phe Pro Ser Ser Val Thr Asn Ser Thr His Ser Leu Leu Pro Gly Thr
        115                 120                 125

Glu Asn Ser Gly Tyr Phe Arg Gly Ser Tyr Ser Asn Ser Pro Ser Asn
    130                 135                 140

Pro Val Asn Ser Arg Ala Asn Gln Asp Phe Ser Ala Leu Met Arg Ser
145                 150                 155                 160

Ser Tyr His Cys Ala Met Asn Asn Glu Asn Ala Arg Leu Leu Thr Phe
                165                 170                 175

Gln Thr Trp Pro Leu Thr Phe Leu Ser Pro Thr Asp Leu Ala Lys Ala
            180                 185                 190

Gly Phe Tyr Tyr Ile Gly Pro Gly Asp Arg Val Ala Cys Phe Ala Cys
        195                 200                 205

Gly Gly Lys Leu Ser Asn Trp Glu Pro Lys Asp Asn Ala Met Ser Glu
    210                 215                 220

His Leu Arg His Phe Pro Lys Cys Pro Phe Ile Glu Asn Gln Leu Gln
225                 230                 235                 240

Asp Thr Ser Arg Tyr Thr Val Ser Asn Leu Ser Met Gln Thr His Ala
                245                 250                 255

Ala Arg Phe Lys Thr Phe Phe Asn Trp Pro Ser Ser Val Leu Val Asn
            260                 265                 270

Pro Glu Gln Leu Ala Ser Ala Gly Phe Tyr Tyr Val Gly Asn Ser Asp
        275                 280                 285

Asp Val Lys Cys Phe Cys Cys Asp Gly Gly Leu Arg Cys Trp Glu Ser
    290                 295                 300

Gly Asp Asp Pro Trp Val Gln His Ala Lys Trp Phe Pro Arg Cys Glu
305                 310                 315                 320

Tyr Leu Ile Arg Ile Lys Gly Gln Glu Phe Ile Arg Gln Val Gln Ala
                325                 330                 335
```

-continued

```
Ser Tyr Pro His Leu Leu Glu Gln Leu Leu Ser Thr Ser Asp Ser Pro
            340                 345                 350

Gly Asp Glu Asn Ala Glu Ser Ser Ile Ile His Phe Glu Pro Gly Glu
            355                 360                 365

Asp His Ser Glu Asp Ala Ile Met Met Asn Thr Pro Val Ile Asn Ala
            370                 375                 380

Ala Val Glu Met Gly Phe Ser Arg Ser Leu Val Lys Gln Thr Val Gln
385                 390                 395                 400

Arg Lys Ile Leu Ala Thr Gly Glu Asn Tyr Arg Leu Val Asn Asp Leu
                405                 410                 415

Val Leu Asp Leu Leu Asn Ala Glu Asp Glu Ile Arg Glu Glu Glu Arg
            420                 425                 430

Glu Arg Ala Thr Glu Glu Lys Glu Ser Asn Asp Leu Leu Leu Ile Arg
            435                 440                 445

Lys Asn Arg Met Ala Leu Phe Gln His Leu Thr Cys Val Ile Pro Ile
    450                 455                 460

Leu Asp Ser Leu Leu Thr Ala Gly Ile Ile Asn Glu Gln Glu His Asp
465                 470                 475                 480

Val Ile Lys Gln Lys Thr Gln Thr Ser Leu Gln Ala Arg Glu Leu Ile
                485                 490                 495

Asp Thr Ile Leu Val Lys Gly Asn Ile Ala Ala Thr Val Phe Arg Asn
            500                 505                 510

Ser Leu Gln Glu Ala Glu Ala Val Leu Tyr Glu His Leu Phe Val Gln
            515                 520                 525

Gln Asp Ile Lys Tyr Ile Pro Thr Glu Asp Val Ser Asp Leu Pro Val
530                 535                 540

Glu Glu Gln Leu Arg Arg Leu Gln Glu Arg Thr Cys Lys Val Cys
545                 550                 555                 560

Met Asp Lys Glu Val Ser Ile Val Phe Ile Pro Cys Gly His Leu Val
                565                 570                 575

Val Cys Lys Asp Cys Ala Pro Ser Leu Arg Lys Cys Pro Ile Cys Arg
            580                 585                 590

Ser Thr Ile Lys Gly Thr Val Arg Thr Phe Leu Ser
            595                 600
```

(2) INFORMATION FOR SEQ ID NO:5:

(i) SEQUENCE CHARACTERISTICS:
        (A) LENGTH: 55 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Cys Glu Leu Tyr Arg Met Ser Thr Tyr Ser Thr Phe Pro Ala Gly Val
1               5                   10                  15

Pro Val Ser Glu Arg Ser Leu Ala Arg Ala Gly Phe Tyr Tyr Thr Gly
            20                  25                  30

Val Asn Asp Lys Val Lys Cys Phe Cys Cys Gly Leu Met Leu Asp Asn
            35                  40                  45

Trp Lys Leu Gly Asp Ser Pro
    50                  55
```

(2) INFORMATION FOR SEQ ID NO:6:

(i) SEQUENCE CHARACTERISTICS:
    (A) LENGTH: 55 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:6:

```
Cys Glu Leu Tyr Arg Met Ser Thr Tyr Ser Thr Phe Pro Ala Gly Val
1               5                   10                  15

Pro Val Ser Glu Arg Ser Leu Ala Arg Ala Gly Phe Tyr Tyr Thr Gly
                20                  25                  30

Val Asn Asp Lys Val Lys Cys Phe Cys Cys Gly Leu Met Leu Asp Asn
            35                  40                  45

Trp Lys Arg Gly Asp Ser Pro
    50                  55
```

(2) INFORMATION FOR SEQ ID NO:7:

(i) SEQUENCE CHARACTERISTICS:
        (A) LENGTH: 46 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

```
Leu Ala Arg Ala Gly Phe Tyr Tyr Ile Gly Pro Gly Asp Arg Val Ala
1               5                   10                  15

Cys Phe Ala Cys Gly Gly Lys Leu Ser Asn Trp Glu Pro Lys Asp Asp
                20                  25                  30

Ala Met Ser Glu His Arg Arg His Phe Pro Asn Cys Pro Phe
            35                  40                  45
```

(2) INFORMATION FOR SEQ ID NO:8:

(i) SEQUENCE CHARACTERISTICS:
        (A) LENGTH: 46 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

```
Leu Ala Lys Ala Gly Phe Tyr Tyr Ile Gly Pro Gly Asp Arg Val Ala
1               5                   10                  15

Cys Phe Ala Cys Gly Gly Lys Leu Ser Asn Trp Glu Pro Lys Asp Asn
                20                  25                  30

Ala Met Ser Glu His Leu Arg His Phe Pro Lys Cys Pro Phe
            35                  40                  45
```

(2) INFORMATION FOR SEQ ID NO:9:

(i) SEQUENCE CHARACTERISTICS:
        (A) LENGTH: 48 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

```
Pro Glu Gln Leu Ala Ser Ala Gly Phe Tyr Tyr Val Gly Arg Asn Asp
1               5                   10                  15

Asp Val Lys Cys Phe Cys Cys Asp Gly Gly Leu Arg Cys Trp Glu Ser
                20                  25                  30

Gly Asp Asp Pro Trp Val Glu His Ala Lys Trp Phe Pro Arg Cys Glu
            35                  40                  45
```

(2) INFORMATION FOR SEQ ID NO:10:

(i) SEQUENCE CHARACTERISTICS:
        (A) LENGTH: 48 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

```
Pro Glu Gln Leu Ala Ser Ala Gly Phe Tyr Tyr Val Gly Asn Ser Asp
1               5                   10                  15

Asp Val Lys Cys Phe Cys Cys Asp Gly Gly Leu Arg Cys Trp Glu Ser
                20                  25                  30

Gly Asp Asp Pro Trp Val Gln His Ala Lys Trp Phe Pro Arg Cys Glu
            35                  40                  45
```

(2) INFORMATION FOR SEQ ID NO:11:

(i) SEQUENCE CHARACTERISTICS:
        (A) LENGTH: 52 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

```
Glu Glu Arg Thr Cys Lys Val Cys Met Asp Lys Glu Val Ser Val Val
1               5                   10                  15

Phe Ile Pro Cys Gly His Leu Val Val Cys Gln Glu Cys Ala Pro Ser
                20                  25                  30

Leu Arg Lys Cys Pro Ile Cys Arg Gly Ile Ile Lys Gly Thr Val Arg
            35                  40                  45

Thr Phe Leu Ser
            50
```

(2) INFORMATION FOR SEQ ID NO:12:

(i) SEQUENCE CHARACTERISTICS:
        (A) LENGTH: 52 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

```
Glu Glu Arg Thr Cys Lys Val Cys Met Asp Lys Glu Val Ser Ile Val
1               5                   10                  15

Phe Ile Pro Cys Gly His Leu Val Val Cys Lys Asp Cys Ala Pro Ser
                20                  25                  30

Leu Arg Lys Cys Pro Ile Cys Arg Ser Thr Ile Lys Gly Thr Val Arg
            35                  40                  45
```

Thr Phe Leu Ser
  50

(2) INFORMATION FOR SEQ ID NO:13:

(i) SEQUENCE CHARACTERISTICS:
        (A) LENGTH: 2862 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

```
TTCCTTTACA GTGAATACTG TAGTCTTAAT AGACCTGAGC TGACTGCTGC AGTTGATGTA     60

ACCCACTTTA GAGAATACTG TATGACATCT TCTCTAAGGA AAACCAGCTG CAGACTTCAC    120

TCAGTTCCTT TCATTTCATA GGAAAAGGAG TAGTTCAGAT GTCATGTTTA AGTCCTTATA    180

AGGGAAAAGA GCCTGAATAT ATGCCCTAGT ACCTAGGCTT CATAACTAGT AATAAGAAGT    240

TAGTTATGGG TAAATAGATC TCAGGTTACC CAGAAGAGTT CATGTGACCC CCAAAGAGTC    300

CTAACTAGTG TCTTGGCAAG TGAGACAGAT TTGTCCTGTG AGGGTGTCAA TTCACCAGTC    360

CAAGCAGAAG ACAATGAATC TATCCAGTCA GGTGTCTGTG GTGGAGATCT AGTGTCAAGT    420

GGTGAGAAAC TTCATCTGGA AGTTTAAGCG GTCAGAAATA CTATTACTAC TCATGGACAA    480

AACTGTCTCC CAGAGACTCG GCCAAGGTAC CTTACACCAA AAACTTAAAC GTATAATGGA    540

GAAGAGCACA ATCTTGTCAA ATTGGACAAA GGAGAGCGAA GAAAAAATGA AGTTTGACTT    600

TTCGTGTGAA CTCTACCGAA TGTCTACATA TTCAGCTTTT CCCAGGGGAG TTCCTGTCTC    660

AGAGAGGAGT CTGGCTCGTG CTGGCTTTTA TTATACAGGT GTGAATGACA AAGTCAAGTG    720

CTTCTGCTGT GGCCTGATGT TGGATAACTG GAAACAAGGG GACAGTCCTG TTGAAAAGCA    780

CAGACAGTTC TATCCCAGCT GCAGCTTTGT ACAGACTCTG CTTTCAGCCA GTCTGCAGTC    840

TCCATCTAAG AATATGTCTC CTGTGAAAAG TAGATTTGCA CATTCGTCAC CTCTGGAACG    900

AGGTGGCATT CACTCCAACC TGTGCTCTAG CCCTCTTAAT TCTAGAGCAG TGGAAGACTT    960

CTCATCAAGG ATGGATCCCT GCAGCTATGC CATGAGTACA GAAGAGGCCA GATTTCTTAC   1020

TTACAGTATG TGGCCTTTAA GTTTTCTGTC ACCAGCAGAG CTGGCCAGAG CTGGCTTCTA   1080

TTACATAGGG CCTGGAGACA GGGTGGCCTG TTTTGCCTGT GGTGGGAAAC TGAGCAACTG   1140

GGAACCAAAG GATGATGCTA TGTCAGAGCA CCGCAGACAT TTTCCCCACT GTCCATTTCT   1200

GGAAAATACT TCAGAAACAC AGAGGTTTAG TATATCAAAT CTAAGTATGC AGACACACTC   1260

TGCTCGATTG AGGACATTTC TGTACTGGCC ACCTAGTGTT CCTGTTCAGC CCGAGCAGCT   1320

TGCAAGTGCT GGATTCTATT ACGTGGATCG CAATGATGAT GTCAAGTGCT TTGTTGTGA    1380

TGGTGGCTTG AGATGTTGGG AACCTGGAGA TGACCCCTGG ATAGAACACG CCAAATGGTT   1440

TCCAAGGTGT GAGTTCTTGA TACGGATGAA GGGTCAGGAG TTTGTTGATG AGATTCAAGC   1500

TAGATATCCT CATCTTCTTG AGCAGCTGTT GTCCACTTCA GACACCCCAG AGAAGAAAA    1560

TGCTGACCCT ACAGAGACAG TGGTGCATTT TGGCCCTGGA GAAAGTTCGG AAGATGTCGT   1620

CATGATGAGC ACGCCTGTGG TTAAAGCAGC CTTGGAAATG GGCTTCAGTA GGAGCCTGGT   1680

GAGACAGACG GTTCAGCGGC AGATCCTGGC CACTGGTGAG AACTACAGGA CCGTCAATGA   1740

TATTGTCTCA GTACTTTTGA ATGCTGAAGA TGAGAGAAGA GAAGAGGAGA AGGAAAGACA   1800

GACTGAAGAG ATGGCATCAG GTGACTTATC ACTGATTCGG AAGAATAGAA TGGCCCTCTT   1860

TCAACAGTTG ACACATGTCC TTCCTATCCT GGATAATCTT CTTGAGGCCA GTGTAATTAC   1920
```

-continued

```
AAAACAGGAA CATGATATTA TTAGACAGAA AACACAGATA CCCTTACAAG CAAGAGAGCT    1980

TATTGACACC GTTTTAGTCA AGGGAAATGC TGCAGCCAAC ATCTTCAAAA ACTCTCTGAA    2040

GGAAATTGAC TCCACGTTAT ATGAAAACTT ATTTGTGGAA AAGAATATGA AGTATATTCC    2100

AACAGAAGAC GTTTCAGGCT TGTCATTGGA AGAGCAGTTG CGGAGATTAC AAGAAGAACG    2160

AACTTGCAAA GTGTGTATGG ACAGAGAGGT TTCTATTGTG TTCATTCCGT GTGGTCATCT    2220

AGTAGTCTGC CAGGAATGTG CCCCTTCTCT AAGGAAGTGC CCCATCTGCA GGGGGACAAT    2280

CAAGGGGACT GTGCGCACAT TTCTCTCATG AGTGAAGAAT GGTCTGAAAG TATTGTTGGA    2340

CATCAGAAGC TGTCAGAACA AAGAATGAAC TACTGATTTC AGCTCTTCAG CAGGACATTC    2400

TACTCTCTTT CAAGATTAGT AATCTTGCTT TATGAAGGGT AGCATTGTAT ATTTAAGCTT    2460

AGTCTGTTGC AAGGGAAGGT CTATGCTGTT GAGCTACAGG ACTGTGTCTG TTCCAGAGCA    2520

GGAGTTGGGA TGCTTGCTGT ATGTCCTTCA GGACTTCTTG GATTTGGAAT TTGTGAAAGC    2580

TTTGGATTCA GGTGATGTGG AGCTCAGAAA TCCTGAAACC AGTGGCTCTG GTACTCAGTA    2640

GTTAGGGTAC CCTGTGCTTC TTGGTGCTTT TCCTTTCTGG AAAATAAGGA TTTTTCTGCT    2700

ACTGGTAAAT ATTTTCTGTT TGTGAGAAAT ATATTAAAGT GTTTCTTTTA AAGGCGTGCA    2760

TCATTGTAGT GTGTGCAGGG ATGTATGCAG GCAAAACACT GTGTATATAA TAAATAAATC    2820

TTTTTAAAAA GTGAAAAAAA AAAAAAAAAA AAAAAAAAA AA                       2862
```

(2) INFORMATION FOR SEQ ID NO:14:

(i) SEQUENCE CHARACTERISTICS:
        (A) LENGTH: 612 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:14:

```
Met Asp Lys Thr Val Ser Gln Arg Leu Gly Gln Gly Thr Leu His Gln
1               5                   10                  15

Lys Leu Lys Arg Ile Met Glu Lys Ser Thr Ile Leu Ser Asn Trp Thr
            20                  25                  30

Lys Glu Ser Glu Glu Lys Met Lys Phe Asp Phe Ser Cys Glu Leu Tyr
        35                  40                  45

Arg Met Ser Thr Tyr Ser Ala Phe Pro Arg Gly Val Pro Val Ser Glu
    50                  55                  60

Arg Ser Leu Ala Arg Ala Gly Phe Tyr Tyr Thr Gly Val Asn Asp Lys
65                  70                  75                  80

Val Lys Cys Phe Cys Cys Gly Leu Met Leu Asp Asn Trp Lys Gln Gly
                85                  90                  95

Asp Ser Pro Val Glu Lys His Arg Gln Phe Tyr Pro Ser Cys Ser Phe
            100                 105                 110

Val Gln Thr Leu Leu Ser Ala Ser Leu Gln Ser Pro Ser Lys Asn Met
        115                 120                 125

Ser Pro Val Lys Ser Arg Phe Ala His Ser Ser Pro Leu Glu Arg Gly
    130                 135                 140

Gly Ile His Ser Asn Leu Cys Ser Ser Pro Leu Asn Ser Arg Ala Val
145                 150                 155                 160

Glu Asp Phe Ser Ser Arg Met Asp Pro Cys Ser Tyr Ala Met Ser Thr
                165                 170                 175
```

```
Glu Glu Ala Arg Phe Leu Thr Tyr Ser Met Trp Pro Leu Ser Phe Leu
            180                 185                 190

Ser Pro Ala Glu Leu Ala Arg Ala Gly Phe Tyr Tyr Ile Gly Pro Gly
        195                 200                 205

Asp Arg Val Ala Cys Phe Ala Cys Gly Gly Lys Leu Ser Asn Trp Glu
    210                 215                 220

Pro Lys Asp Asp Ala Met Ser Glu His Arg Arg His Phe Pro His Cys
225                 230                 235                 240

Pro Phe Leu Glu Asn Thr Ser Glu Thr Gln Arg Phe Ser Ile Ser Asn
                245                 250                 255

Leu Ser Met Gln Thr His Ser Ala Arg Leu Arg Thr Phe Leu Tyr Trp
                260                 265                 270

Pro Pro Ser Val Pro Val Gln Pro Glu Gln Leu Ala Ser Ala Gly Phe
            275                 280                 285

Tyr Tyr Val Asp Arg Asn Asp Asp Val Lys Cys Phe Cys Cys Asp Gly
        290                 295                 300

Gly Leu Arg Cys Trp Glu Pro Gly Asp Asp Pro Trp Ile Glu His Ala
305                 310                 315                 320

Lys Trp Phe Pro Arg Cys Glu Phe Leu Ile Arg Met Lys Gly Gln Glu
                325                 330                 335

Phe Val Asp Glu Ile Gln Ala Arg Tyr Pro His Leu Leu Glu Gln Leu
            340                 345                 350

Leu Ser Thr Ser Asp Thr Pro Gly Glu Glu Asn Ala Asp Pro Thr Glu
        355                 360                 365

Thr Val Val His Phe Gly Pro Gly Glu Ser Ser Glu Asp Val Val Met
    370                 375                 380

Met Ser Thr Pro Val Val Lys Ala Ala Leu Glu Met Gly Phe Ser Arg
385                 390                 395                 400

Ser Leu Val Arg Gln Thr Val Gln Arg Gln Ile Leu Ala Thr Gly Glu
                405                 410                 415

Asn Tyr Arg Thr Val Asn Asp Ile Val Ser Val Leu Leu Asn Ala Glu
            420                 425                 430

Asp Glu Arg Arg Glu Glu Glu Lys Glu Arg Gln Thr Glu Glu Met Ala
        435                 440                 445

Ser Gly Asp Leu Ser Leu Ile Arg Lys Asn Arg Met Ala Leu Phe Gln
    450                 455                 460

Gln Leu Thr His Val Leu Pro Ile Leu Asp Asn Leu Leu Glu Ala Ser
465                 470                 475                 480

Val Ile Thr Lys Gln Glu His Asp Ile Ile Arg Gln Lys Thr Gln Ile
                485                 490                 495

Pro Leu Gln Ala Arg Glu Leu Ile Asp Thr Val Leu Val Lys Gly Asn
            500                 505                 510

Ala Ala Ala Asn Ile Phe Lys Asn Ser Leu Lys Glu Ile Asp Ser Thr
        515                 520                 525

Leu Tyr Glu Asn Leu Phe Val Glu Lys Asn Met Lys Tyr Ile Pro Thr
    530                 535                 540

Glu Asp Val Ser Gly Leu Ser Leu Glu Glu Gln Leu Arg Arg Leu Gln
545                 550                 555                 560

Glu Glu Arg Thr Cys Lys Val Cys Met Asp Arg Glu Val Ser Ile Val
                565                 570                 575

Phe Ile Pro Cys Gly His Leu Val Cys Gln Glu Cys Ala Pro Ser
            580                 585                 590

Leu Arg Lys Cys Pro Ile Cys Arg Gly Thr Ile Lys Gly Thr Val Arg
```

```
                  595                 600                 605
Thr Phe Leu Ser
    610
```